United States Patent [19]

Sterling et al.

[11] Patent Number: 4,900,814

[45] Date of Patent: Feb. 13, 1990

[54] SYNTHESIS OF PODOPHYLLOTOXIN DERIVATIVES

[76] Inventors: Jeffrey Sterling, 156/1 Ramot, Jerusalem; Abraham Nudelman, 15 Miller Street, Rehovot; Jaacov Herzig, 7 Hashiryon Street, Raanana; Ehud Keinan, 30 Efal Street, Holon; Ben Z. Weiner, 306 Hapartisanim Flat No. 16, Nevo, Jerusalem, all of Israel

[21] Appl. No.: 943,203

[22] Filed: Dec. 15, 1986

[30] Foreign Application Priority Data

Dec. 16, 1985 [IL] Israel ........................................ 77334

[51] Int. Cl.$^4$ ............................................. C07H 15/24
[52] U.S. Cl. ..................... 536/18.1; 536/4.1; 536/18.5; 536/18.6; 536/124
[58] Field of Search .................. 536/18.1, 18.5, 18.6, 536/124, 4.1

[56] References Cited

U.S. PATENT DOCUMENTS

| | | | |
|---|---|---|---|
| 4,564,675 | 1/1986 | Kurabayashi et al. | 536/4.1 |
| 4,609,644 | 9/1986 | Nemec | 536/4.1 |
| 4,757,138 | 7/1988 | Fujii et al. | 536/4.1 |

FOREIGN PATENT DOCUMENTS

| | | | |
|---|---|---|---|
| 61-56193 | 3/1986 | Japan | 536/4.1 |
| 8600018 | 1/1986 | PCT Int'l Appl. | 536/18.5 |

Primary Examiner—Ronald W. Griffin
Assistant Examiner—Nancy S. Carson
Attorney, Agent, or Firm—Browdy and Neimark

[57] ABSTRACT

There is provided a novel process for the production of the epipodophyllotoxin glycosides, Etoposide and Teniposide. There are further provided certain novel 4′-demethylepipodophyllotoxin derivatives of the following formula

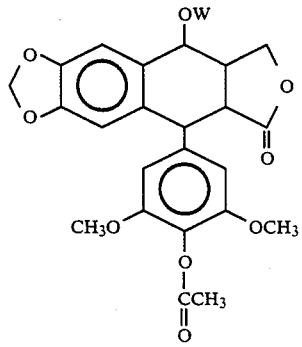

where W is hydrogen or 2,3-di-O-acetyl-4,6,O-ethylidene-D-glucopyran-1-yl. These intermediates are easily transformed into Etoposide and Teniposide and into further derivatives of this series.

9 Claims, No Drawings

SYNTHESIS OF PODOPHYLLOTOXIN DERIVATIVES

BACKGROUND OF THE INVENTION

Certain glycosides of podophyllotoxin, and more specifically Etoposide and Teniposide, are widely used in human medicine as anti-cancer agents. They are of special value in the treatment of small-cell lung cancer and of testicular cancer. (Clin. Pharmacy, 2, 112 (1983)). The conventional processes for the production of these products are rather complicated and expensive, and there exists a need for a simple inexpensive process of production. Etoposide has been prepared by the reaction of 4′ carbobenzoxy-4′-demethylepipodophyllotoxin and 2,3-di-O-acetyl 4,6,0-ethylidene-D-glucopyranose; (Swiss Patent No. 514578). Tenoposide has been prepared by the reaction of the 4′-carbobenzoxy-4′-demethylepidodophyllotoxin with 2,3,4,6-tetra-O-acetyl-glucopyranose (Israel patent No. 34853). The starting carbobenzoxy compound can be prepared from podophyllotoxin according to Israel patent No. 26522.

According to Swiss Patent No. 514578, after the condensation reaction, the carbobenzoxy and acetoxy protecting groups must be removed separately from the resulting glycoside in order to isolate Etoposide and furthermore a thienylidene group must be added to prepare Teniposide (U.K. Patent No. 823,068). The reaction sequence outlined above has drawbacks and it is extremely difficult to produce Etoposide or Teniposide on an industrial scale. Among the disadvantages are:

1. The need for the expensive and dangerous reagent benzylchloroformate and the precise reaction conditions in order to selectively protect the phenolic hydroxy group.
2. The need for two separate chemical reaction steps to remove the two different protecting groups from the condensation product.
3. The synthesis of the required glucose intermediates involves a complex multistep process requiring strict control of reaction conditions. Furthermore, each of the sugars has a free hydroxyl group in the anomeric position making them liable to anomerization. The method of Kuhn and von Wartburg (Helv.Chim. .Acta, 52, 948 (1969), requires that the sugars be in the β-form. The α-anomer will give and -glycoside as condensation product which is not useful in the synthesis of Etoposide, which is a β-glycoside. The u-form of these sugars is the thermodynamically more stable form and tends to be formed rapidly even under mild equilibrium conditions.

The process of the present invention overcomes to a large extent the drawbacks of conventional processes for the production of Etoposide and Teniposide.

SUMMARY OF THE INVENTION

There is provided a process for the production of glycosides of podophyllotoxin and especially of the pharmaceutically important glycosides Etoposide and Teniposide which are widely used as anti-cancer drugs.

There are further provided novel intermediates for use in such synthesis.

The process of the invention comprises reacting a compound of Formula I with a compound of Formula 11 in the presence of a Lewis Acid, such as boron trifluoride, to yield a compound of Formula III

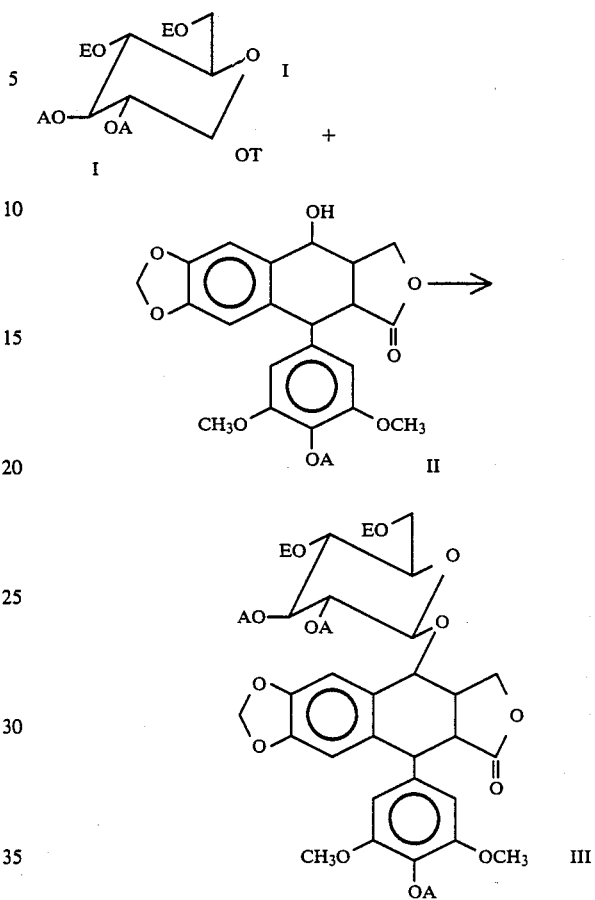

where:

In Formula I, T designates tri-alkyl tin, and preferably tri-n-butyl tin; A designates a lower alkanoyl group or lower chloroalkanoyl group, preferably acetyl or chloroacetyl; and E designates also lower alkanoyl or lower chloroalkanoyl, preferably acetyl or chloroacetyl or both groups E designate together an ethylidene group.

In Formula II, A is the same as in Formula I.

In Formula III, A and E are as defined above. The 4′-demethylepipodophyllotoxin of Formula II where A is lower alkanoyl, is a novel compound.

The compounds of Formula III where A is acetyl and where E is loweralkanoyl or both E together define an ethylidene group are also novel compounds.

According to a specific embodiment of the invention a compound of the Formula IV.

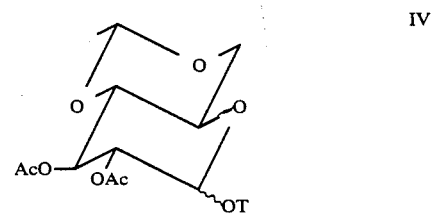

where Ac is acetyl and T is as defined above, is reacted with a compound of Formula II where A is acetyl, to result in a compound of Formula V

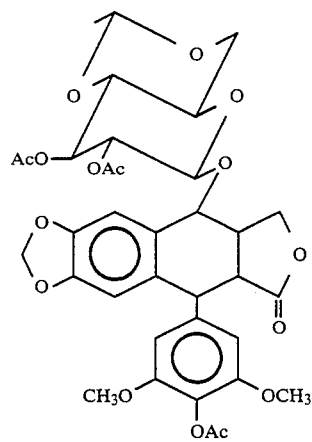

which is a novel compound. This compound is a precursor of Etoposide.

The reaction of the compounds of Formula IV and II is catalysed by Lewis acids, and the compound of choice is boron trifluoride. The novel intermediate of Formula V is readily converted to Etoposide. This is done by removal of the acetyl protective groups with zinc acetate in an alcoholic solvent to yield Etoposide.

The intermediate VII for Teniposide has been prepared in an analagous manner, using the glucose intermediate VI instead of IV to give a compound of Formula VII in formulas IV, VI and VII AC is acetyl.

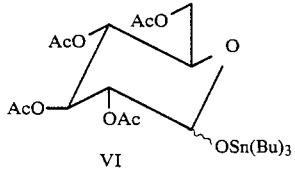

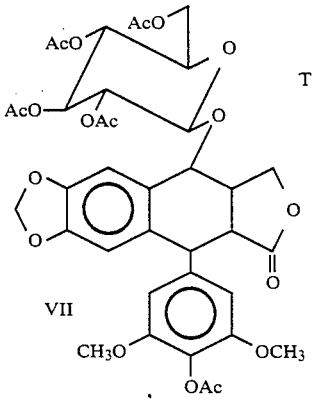

The important intermediate, Compound I, is prepared from Compound VIII, wherein A and E and T are as defined above, in Formula I by reaction with a tri-alkyl tin compound of the formula $(R)_3$-SnO-R' where R and R' are each lower alkyl. The preferred compound is $(n.Bu)_3$ $SnOCH_3$.

Other suitable tin compounds are $(R_3Sn)_2O$ and $(Bu_3Sn)_2O$, the preferred one being $(Bu_3Sn)_2O$.

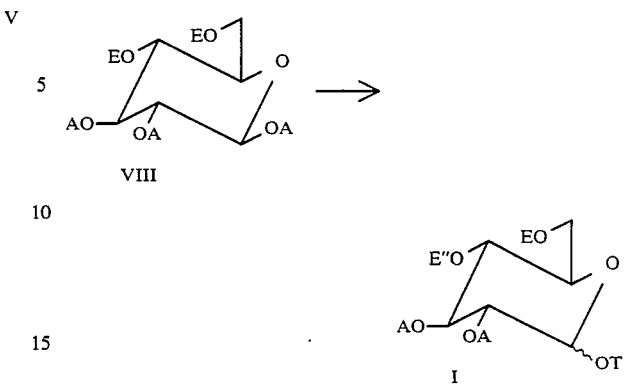

According to the method of the invention, a compound of Formula II is prepared from compound X. Compound X is prepared by treating a solution of IX

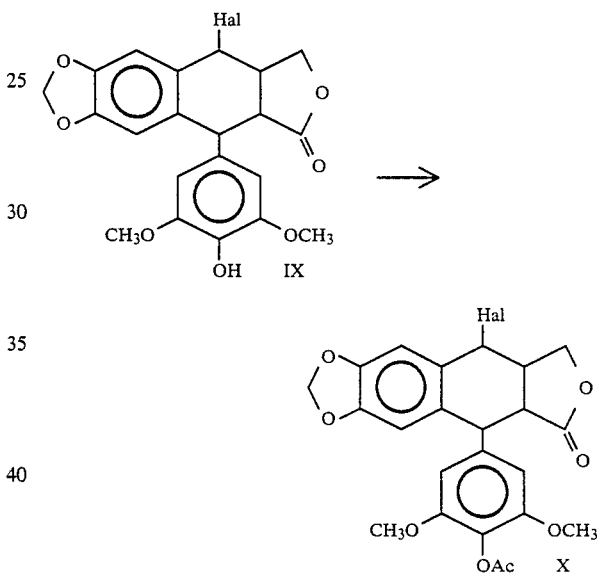

where Hal is a halogen preferably bromine and Ac is acetyl, in a suitable inert solvent, preferably a chlorinated hydrocarbon such as methylene chloride, with an excess of a suitable acetylating agent, preferably acetyl chloride n the presence of a tertiary amine base, preferably pyridine. The temperature of the reaction is in the range of −20° to 25° and the period of the reaction from 1.5 to 12 hours, preferably about 20° C. for about 2-3 hours. By performing the reaction to protect the phenolic hydroxy group at this stage in the procedure before the hydrolysis of the halogen to hydroxy group, the necessity to choose a protecting process that is selective for a phenolic hydroxy in the presence of a benzylic hydroxy has been avoided. For this reason the acetate can be used as the protecting group, despite the fact that acetyl chloride or other acetylating reagents are not selective for a phenolic hydroxy in the presence of other hydroxy groups in the same molecule.

Hydrolysis of the halogen of compound X is accomplished by heating in a mixed aqueous-organic solvent system. Preferred organic solvents for the reaction are acetone or acetonitrile, preferably in a 1:1 ratio with water. The temperature of reaction is preferably between 40° C. and the reflux temperature of the mixture. The period of the reaction is about 1 hour.

It has been surprisingly found that neither barium carbonate, as required by Israeli patent No. 26522 for an analogous transformation, nor any other base, is necessary for the hydrolysis of the halide in X to the hydroxy compound II where A is acetyl.

The omission of barium carbonate from this reaction greatly facilitates the work-up procedure. The preparation of 11 where A is chloroacyl has been described in European Patent Application No. 111058. The use of acetate or chloroacetate as a phenolic hydroxy protecting group is of great advantage in the process of this invention, as will become apparent thereafter.

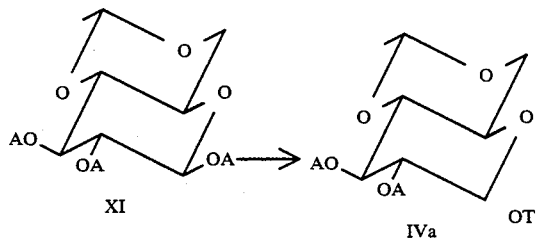

The glucose derivative IVa is prepared by reacting a compound of the formula XI wherein A is as defined above, with a suitable tri-alkyl tin derivative of the formula (R)$_3$-Sn-O-R' where R is lower alkyl as defined above and preferably n-Bu$_3$ and where R' is the same or a different lower alkyl, preferably methyl, or SnR$_3$ where R is as defined above, in a suitable aprotic inert solvent.

A preferable solvent for the reaction is methylene chloride, dichloroethane, toluene, etc. The preferable temperature for the reaction is from 0° C. to the reflux temperature of the solvent. The period of the reaction is from about 30 min. to 48 hours, depending on the reaction temperature.

The preferred embodiment of the reaction utilizes a trialkyl tin derivative of the form (R)$_3$ Sn-OCH$_3$, because then the tin-glucose derivative IV may be isolated in relatively pure form simply by removing the volatile substances from the reaction mixture, preferably under reduced pressure.

Despite the fact that XI is the anomerically pure β anomer, the resulting compound IV in oil form, is a mixture of the α- and β-anomers in approximately equal amounts. Pure α-anomer may be isolated from the mixture by recrystallization from a hexane solution of the mixed anomers.

However, the anomeric purity and identity of intermediate IV has surprisingly been found to be irrelevant to the purposes of this invention. Thus, when V is prepared according to the process of the invention, by treating a solution of IV and II in an inert solvent, preferably a chlorinated hydrocarbon such as dichloroethane, with boron trifluoride etherate at a temperature of 0° C. to 25° C., the desired β-glycoside V is the predominant reaction product regardless of the anomeric identity of the glucose intermediate IV.

Thus according to the preferred embodiment of this invention a crude anomeric mixture IV is used for the condensation reaction. However, even if the Pure crystalline α-anomer is used, the surprising and unexpected reaction product is almost exclusively the β-glycoside V. This result is in contrast with the condensation reaction between II and a glucose derivative with a free anomeric hydroxyl such as 2,3-di-O-acetyl-4,6-O-ethylidene-D-glucopyranose. In this case, the anomeric purity of the resulting glycoside is a reflection of the purity of the above glucose reagent. Because of the difficulty in isolating this free hydroxy glucose in the pure β-form, and its instability, the use of IV as an analogous intermediate is clearly preferred.

According to a further embodiment of the invention, the acid catalyst of the condensation reaction is neutralized with a mild aqueous base, such as sodium bicarbonate, and thus the decomposition of the boron trifluoride etherate generates fluoride ions which react with the tributyltin residue, forming tributyltin fluoride which precipitates out of the reaction mixture and is readily removed by filtration This is the preferred method for the removal of the tri-n-butyltin residue from the reaction mixture.

Compound V is readily converted into etoposide by the removal of the three acetate protecting groups with zinc acetate in an alcoholic solvent, in analogy with Swiss Patent No. 514578. Moreover, such treatment removes all the protecting groups of V, including the phenolic acetate which has replaced the carbobenzoxy group used hitherto as a protecting group. Thus, no additional catalytic hydrogenation step or other deprotection step is needed and the sample treatment with zinc acetate removes all the protecting groups, yielding directly Etoposide.

A compound of the formula VII may be similarly deacetylated in a single reaction and the resulting intermediate reacted with 2-thiophene carboxaldehyde according to British patent 823,068 to give Teniposide.

The use of chloracyl instead of acyl protecting groups, for example as in Formula III where A and E are as defined, enables deprotection under even milder conditions (see European Patent Application No. 11058).

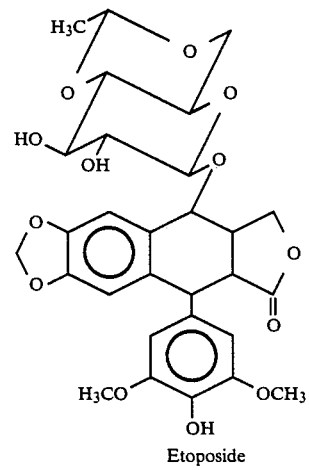

Etoposide

-continued

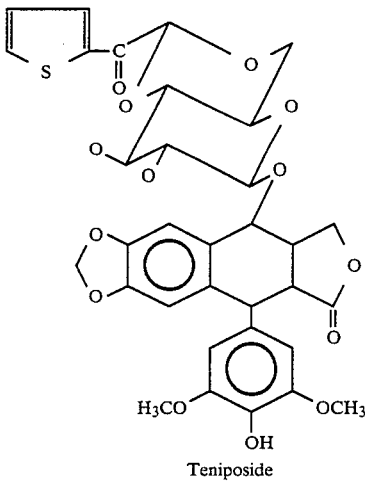
Teniposide

EXAMPLE 1

Tri-n-Butyltin-(2,3-di-O-acetyl-4,6,0-Ethylidene)-D-Glucopyranoside(IV)

To a solution of 133 g of 1,2,3-tri-0-acetyl-4,6-O-ethylidene-$\beta$-D-glucopyranose (0.4 mole) in 600 ml of dichloroethane under nitrogen atmosphere was added 115 ml (0.4 mole) of tri-n-butyltin methoxide. The resulting solution was coated at reflux for 1 hour. Removal of the volatiles in vacuo yielded the title compound in 100% yield as a mixture of the $\alpha$ and $\beta$ anomers.

Pure tri-n-butyltin-(2,3-di-O-acetyl-4,6-O-ethylidene)-$\alpha$-D-glucopyranoside can be isolated from this mixture by recrystallization from hexane. Melting point: 82°–85°. Anal. calcd. for $C_{24}H_{41}O_8Sn$: C, 50.03; H, 7.17. Found: C, 50.22; H, 7.47. NMR ($\delta$, $CDCl_3$): 5.52 (t, 1H), 2.07 (s, 3H), 2.05 (s,3H), 0.91 (t, 9H).

EXAMPLE 2

Tri-n-Butyltin-(2,3,4,6-tetra-O-acetyl-D-Glucopyranoside(VI).

The title compound was obtained in direct analogy with the method of Example 1 except that 1,2,3,4,6-penta-O-acetyl-$\beta$-D-glucopyranose was used. High resolution mass spec fragment [M - $C_4H_9$] calcd for $C_{22}H_{37}O_{10}{}^{118}Sn$ 579 1402. Found 579.1398 (100%). Calcd. for $C_{22}H_{37}O_{10}{}^{120}Sn$ 581.1408. Found 581.1377 (100%).

EXAMPLE 3

1,2,3-Tri-0-Chloroacetyl-4,6-0 Ethylidene-D-Glucopyranose

To a mixture of 31 g of chloroacetic anhydride and 2.4 g of sodium acetate at 70° was added 5 g of 4,6-O-ethylidene glucose with stirring. After one hour at that temperature the reaction mixture was poured into ice, diluted with methylene chloride and ammonium hydroxide was added until basic. The organic phase was separated, dried over $MgSO_4$ and concentrated in vacuo. The residue was recrystallized from ether to give the title compound in 44% yield, M.P.=115°–120°. Anal. Calcd for: $(C_{14}H_{17}Cl_3)_9$; C, 38.58; H, 3.93; Cl. 24.44: Found: C, 38.50., H, 4.06., Cl, 24.23.

EXAMPLE 4

Tri-n-Butyltin-(2,3-di-O-Chloroacetyl-4,6-O-Ethylidene)-D-Glucopyranoside

To a solution of 1.0 g of 1,2,3-tri-O-chloroacetyl-4,6-O-ethylidene-D-glucopyranose in 10 ml of dichloroethane under a nitrogen atmosphere was added 0.49 g of tri-n-butyltin methoxide. The resulting solution was heated at reflux for 30 minutes. Removal of volatiles in vacuo yielded the title compound as a mixture of $\alpha$ and $\beta$ anomers. Mass spec: [M-$C_4H_9$]$^+$: $C_{20}H_{33}O_8Cl_2{}^{118}Sn$, 588 6 (1.08%); $C_{20}H_{33}O_8Cl_2$ $^{120}Sn$, 590.5 (1.42%); $C_{20}H_{33}O_8Cl_2{}^{122}Sn$, 592.5 (1.01%). NMR($CDCl_3,\delta$): H-1$\alpha$, 5.36(d); H-1$\beta$, 4.88(d); H-3$\alpha$, 5.58(t); H-3$\beta$, 5.25(t).

EXAMPLE 5

4'-Acetyl-4'-Demethylepipodophyllotoxin (II)

To a stirred solution of 10 ml of pyridine in 150 ml of methylene chloride protected by a calcium chloride drying tube was added rapidly 15.5 g (30.7 mmol) of solid 4'-demethylepipodophyllotoxin bromide. A solution of 4.4 ml (62 mmol) of acetyl chloride in 10 ml of methylene chloride was added dropwise to the resulting dark mixture. After 90 minutes the reaction mixture was washed successively twice with 5% aqueous hydrochloric acid and once with saturated aqueous sodium bicarbonate. Solvent removal in vacuo after drying over sodium sulfate gave 4'-acetyl-4'-demethylepipodophyllotoxin bromide which contained a quantity of the title compound. Hydrolysis of the bromide was completed by treating an acetone (50 ml) solution of the above compound with 50 ml of water and heating the resulting mixture at 45°–55° with vigorous stirring for 1 hour at which time most of the acetone was removed by distillation in vacuo and the title compound was isolated by suction filtration of the resulting aqueous suspension. Purification by recrystallization from methylene chloride/methanol gave an analytical sample, M.P.=261°–264°. Anal. calcd. for $C_{23}H_{22}O_9$: C, 62.44; H, 5.01. Found: C, 62.48; H, 5.18. NMR ($\delta$, $CDCl_3$): 6.87 (s, 1H), 6.56 (s, 1H), 6.31 (s, 2H), 5.98 (d, 2H), 2.30 (s, 3H).

EXAMPLE 6

2,3Di-O-Acetyl-4,6-O-Ethylidene-(4'-Acetyl-4'-Demethylepipodophyllotoxin)-$\beta$-D-Glucopyroanoside(V).

To a stirred suspension of 8.8 g (20 mmol) of 4'-acetyl-4'demethylepipodophyllotoxin from Example 5 and 23.5 g (40 mmol) of tri-n-butyltin-(2,3-di-O-acetyl-4,6-O-ethylidene)-D-glucopyranoside from Example 1 in 60 ml of dichloroethane under a nitrogen atmosphere was added dropwise 7.4 ml of freshly distilled boron trifluoride etherate. The resulting solution was stirred at room temperature for 1 hour and then cautiously treated with a saturated aqueous solution of sodium bicarbonate until no further reaction was noted. The precipitate was separated by suction filtration and washed with methylene chloride until white. The two phases of the filtrate were separated and the organic layer washed once with a 20% aqueous solution of sodium fluoride. The resulting organic layer was again separated, dried over sodium sulfate, and volatiles were removed in vacuo. Column chromatography on silica gel, eluting with a 50/50 mixture of ethyl acetate/hexane, further modified with 5% acetonitrile, gave the title compound which was recrystallized from methylene chloride/methanol. M.P.=265°-268°. Anal.calcd. for $C_{35}H_{38}O_{16}$: C, 58.82; H, 5.36. Found: C, 58.94; H, 5.41. NMR ($\delta$, $CDCl_3$) 6.78 (s, 1H), 6.27 (s, 2H), 5.99 (d, 2H), 2.30 (s, 3H), 2.06 (s, 3H), 1.84 (s, 3H).

EXAMPLE 7

2,3,4,6-Tetra-O-Acetyl-(4'-Acetyl-4'-Demethylepipodophyllotoxin)-$\beta$-D-Glucopyranoside(VII).

To a stirred suspension of 5 g (11 mmol) of 4'-acetyl-4'-demethylepipodophyllotoxin from Example 5 and 14 g (26mmol) of tri-n-butyltin-(2,3,4,6-tetra-O-acetyl)-D-glucopyranoside from Example 2 in 40 ml of dichloroethane, under nitrogen atmosphere was added dropwise 4 ml of freshly distilled boron trifluoride etherate. The resulting solution was stirred at room temperature for 1 hour and then cautiously treated with a saturated aqueous solution of sodium bicarbonate until no further reaction was noted. The precipitate was separated by suction filtration and washed with methylene chloride until white. The two phases of the filtrate were then separated and the organic layer washed once with a 20% aqueous solution of sodium fluoride. The resulting organic layer was again separated, dried over sodium sulfate and volatiles were removed in vacuo.

Column chromatography on silica gel, eluting with diethyl ether/methylene chloride (1/9), gave the title compound which was recrystallized from ethyl acetate/ether as the hemihydrate. M.P.=140°-143°. Anal.calcd. for $C_{37}H_{40}O_{18}\cdot\frac{1}{2}H_2O$. C,56.84; H, 5.29. Found: C, 56.54; H, 5.05. NMR ($\delta$, $CDCl_3$) 6.85 (s, 1H), 6.59 (s, 1H), 6.27 (s, 2H), 5.99 (d, 2H), 2.30 (s, 3H), 2.15 (s, 3H), 2.05 (s, 3H), 2.01 (s, 3H), 1.89 (s, 3H).

EXAMPLE 8

4,6-O-Ethylidene-(4'-Demethylepipodophyllotoxin)-$\beta$-D-Glucopyranoside

A suspension of 11 g(16.3 mmol)of 2,3-di-O-acetyl-4,6-O-ethylidene-(4'-acetyl-4'-demethylepipodophyllotoxin)-$\beta$-D-glucopyranoside from Example 6 in 100 ml of methanol was treated with 10.5 g (50 mmol) of zinc acetate dihydrate. The resulting suspension was heated under reflux for 48 hours at which time the reaction mixture was allowed to cool and 7.2 ml of acetic acid was added. Most of the volatiles were removed in vacuo and the residue suspended in 50 ml of 4:1 chloroform: sec.-butanol which was then treated with 20 ml of water. The resulting precipitate was removed by suction filtration and washed with additional solvent mixture. The two phases of the filtrate were separated and the aqueous layer extracted again with additional solvent mixture. The combined organic layers were washed with aqueous ammonium hydroxide until basic and dried over sodium sulfate. Volatiles were removed in vacuo and the residue was purified by column chromatography on silica gel, eluting with 50:50 methylene chloride: ethyl acetate modified with an increasing gradient of 0-10% acetone. The title compound was recrystallized from chloroform. M.P.=275°-276°. High resolution mass spec calcd for $C_{29}H_{32}O_{13}$, 588.1842. Found: 588.1799 (5%).

We claim:

1. A process for the production of podophyllotoxin derivatives of formula III

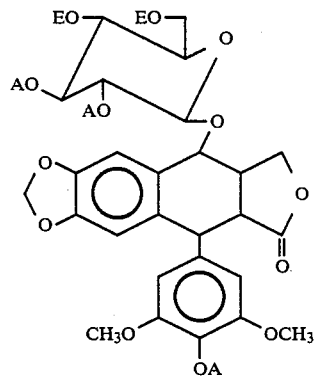

which comprises reacting a molar excess of a glucose derivative of formula I

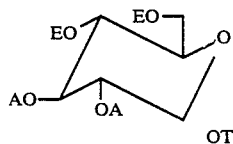

with a 4,'-demethylpipodphyllotoxin derivative of formula II

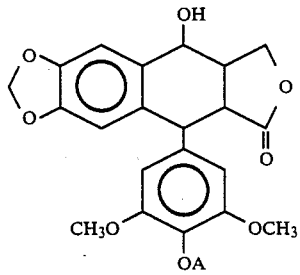

in a chlorinated hydrocarbon solvent in the presence of boron trifluoride at a temperature in the range of from −20° C. to 25° C., where:
T designates tri-lower-alkyl tin,
A designates alkanoyl or chloroalkanoyl of 1 to 5 carbon atoms, and
E is identical with A, or both E groups together designate an ethylidene group.

2. A process according to claim 1, further comprising removing groups A and E when these groups designate acetyl by reacting the product of said process with zinc acetate.

3. A process according to claim 1, wherein in formula I, T designates tri-n-butyl tin.

4. A process according to claim 1, wherein A and E each designate acetyl.

5. A process according to claim 1, wherein A and E each designate chloroacetyl.

6. A process according to claim 1, wherein in formula I, A is acetyl and the E groups together are ethylidene.

7. A process according to claim 1, wherein in formula I, A is chloroacetyl and the E groups together are ethylidine.

8. A process according to claim 2, wherein in formula I, A is chloroacetyl and the E groups together are ethylidine.

9. A process according to claim 3, wherein in formula I, A is chloroacetyl and the E groups together are ethylidine.

* * * * *